US012376935B2

(12) United States Patent
Suzuki et al.

(10) Patent No.: US 12,376,935 B2
(45) Date of Patent: Aug. 5, 2025

(54) SURGERY-ASSISTING DEVICE (71) Applicant: RIVERFIELD INC., Tokyo (JP)

(72) Inventors: Masataka Suzuki, Tokyo (JP); Masao Kanazawa, Tokyo (JP); Kotaro Tadano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 553 days.

(21) Appl. No.: 17/890,394

(22) Filed: Aug. 18, 2022

(65) Prior Publication Data

US 2022/0401175 A1 Dec. 22, 2022

Related U.S. Application Data

(63) Continuation of application No. PCT/JP2020/035331, filed on Sep. 17, 2020.

(30) Foreign Application Priority Data

Feb. 20, 2020 (JP) .................. 2020-027048

(51) Int. Cl.
*A61B 90/00* (2016.01)
*A61B 17/00* (2006.01)
(Continued)

(52) U.S. Cl.
CPC .............. *A61B 90/03* (2016.02); *A61B 34/30* (2016.02); *A61B 90/50* (2016.02);
(Continued)

(58) Field of Classification Search
CPC ......... A61B 90/03; A61B 34/30; A61B 90/50; A61B 2090/032; A61B 2017/00398; A61B 2017/00544; B25J 9/0087; B25J 9/009
(Continued)

(56) References Cited

U.S. PATENT DOCUMENTS

| 4,921,393 A | 5/1990 | Andeen et al. |
| 2007/0013336 A1 | 1/2007 | Nowlin et al. |

(Continued)

FOREIGN PATENT DOCUMENTS

| CN | 101227870 A | 7/2008 |
| CN | 102764159 A | 11/2012 |

(Continued)

OTHER PUBLICATIONS

Office Action dated Dec. 1, 2022 from the Chinese Patent Office in Application No. 202080096931.X.

(Continued)

*Primary Examiner* — T. Scott Fix (74) *Attorney, Agent, or Firm* — Sughrue Mion, PLLC (57) ABSTRACT

A surgery-assisting device includes a robot arm that includes plural movable bodies that are operably connected in order in a connecting direction, a surgical instrument connected to a distal end of the robot arm, and one or more actuators that generate a driving force that operates one or more of the movable bodies. The movable bodies include one or more distal-side movable bodies that is provided distally in the connection direction, and one or more proximal-side movable bodies that is provided proximally in the connection direction. An operation tolerance of the one or more distal-side movable bodies is higher than an operation tolerance of the one or more proximal-side movable bodies.

20 Claims, 6 Drawing Sheets

(51) Int. Cl.
*A61B 34/30* (2016.01)
*A61B 90/50* (2016.01)

(52) U.S. Cl.
CPC .............. *A61B 2017/00398* (2013.01); *A61B 2017/00544* (2013.01); *A61B 2090/032* (2016.02)

(58) Field of Classification Search
USPC ....................................................... 74/490.01
See application file for complete search history.

(56) References Cited

U.S. PATENT DOCUMENTS

| | | |
|---|---|---|
| 2007/0138992 A1 | 6/2007 | Prisco et al. |
| 2011/0282356 A1 | 11/2011 | Solomon et al. |
| 2014/0316436 A1 | 10/2014 | Bar et al. |
| 2015/0045814 A1 | 2/2015 | Prisco et al. |
| 2016/0331482 A1 | 11/2016 | Hares |
| 2017/0181806 A1 | 6/2017 | Itkowitz et al. |
| 2018/0079090 A1 | 3/2018 | Koenig et al. |
| 2019/0110850 A1 | 4/2019 | Hares et al. |
| 2019/0117320 A1 | 4/2019 | Shoham et al. |
| 2020/0197108 A1 | 6/2020 | Usui |
| 2021/0121253 A1* | 4/2021 | Leibrandt .............. B25J 9/0072 |
| 2021/0298858 A1 | 9/2021 | Hares et al. |

FOREIGN PATENT DOCUMENTS

| | | |
|---|---|---|
| CN | 107666875 A | 2/2018 |
| CN | 108472028 A | 8/2018 |
| CN | 108697415 A | 10/2018 |
| CN | 109303610 A | 2/2019 |
| CN | 110638500 A | 1/2020 |
| JP | 2002-017752 A | 1/2002 |
| JP | 2009-131446 A | 6/2009 |
| JP | 2018-516656 A | 6/2018 |
| JP | 2018-198750 A | 12/2018 |
| JP | 2019-013445 A | 1/2019 |
| JP | 2019-141721 A | 8/2019 |
| KR | 10-1911525 B1 | 10/2018 |
| WO | 2006124390 A2 | 11/2006 |
| WO | 2016/181164 A1 | 11/2016 |
| WO | 2017122202 A1 | 7/2017 |
| WO | 2018053349 A1 | 3/2018 |

OTHER PUBLICATIONS

International Search Report for PCT/JP2020/035331 dated Nov. 24, 2020.
Written Opinion for PCT/JP2020/035331 dated Nov. 24, 2020.

* cited by examiner

SURGERY-ASSISTING DEVICE

CROSS-REFERENCE TO RELATED APPLICATIONS

This U.S. Application is a continuation application of International Application No. PCT/JP2020/035331, filed Sep. 17, 2020, which is based on and claims priority to Japanese Patent Application No, 2020-027048 filed on Feb. 20, 2020 with the Japan Patent Office, the contents of each of which being incorporated by reference herein in their entireties.

BACKGROUND

The present disclosure relates to a surgery-assisting device including a plurality of movable bodies that are operably connected to one another in order and actuators that generate driving forces for operating the movable bodies.

In recent years, surgical operations using surgery-assisting devices have come into widespread use. A surgery-assisting device includes an arm that is attached to a surgical instrument that is partly inserted into the body cavity of a patient to perform an operation. In the surgical operation using the surgery-assisting device, it is important not only to enhance the safety of the surgery but also to enhance the accuracy of the surgery. In order to enhance the accuracy of the surgery, it is necessary to precisely control a position and pose of the surgery-assisting device and to enhance positional accuracy at a distal end portion of a surgical instrument inserted in the body cavity.

SUMMARY

It is an aspect to achieve an improvement in safety without causing a rise in manufacturing cost of the surgery-assisting device, and to achieve an improvement in positional accuracy at a distal end portion of a surgical instrument.

According to an aspect of one or more embodiments, there is provided a surgery-assisting device comprising a plurality of movable bodies that are operably connected in order in a connecting direction; and at least one actuator that is configured to generate a driving force that operates at least one of the plurality of movable bodies, wherein one of the plurality of movable bodies that is positioned at one end in the connecting direction of the plurality of movable bodies includes a holding portion configured to hold a surgical instrument, at least one of the plurality of movable bodies that is positioned on a side of the surgical instrument in the connecting direction and that includes the one of the plurality of movable bodies having the holding portion is provided as a distal-side movable body, at least one of the plurality of movable bodies that includes a movable body positioned farthest from the surgical instrument in the connecting direction and that is other than the distal-side movable body is provided as a proximal-side movable body, and an operation tolerance of the distal-side movable body is higher than the operation tolerance of the proximal-side movable body, the operation tolerance being a degree of tolerance for operation of a movable body at a time when an external force other than the driving force of the at least one actuator is applied to the movable body.

According to another aspect of one or more embodiments, there is provided a surgery-assisting device comprising a robot arm comprising a plurality of movable bodies that are operably connected in order in a connection direction; a surgical instrument connected to a distal end of the robot arm; and at least one actuator that is configured to generate a driving force that operates at least one of the plurality of movable bodies, wherein the plurality of movable bodies comprises at least one distal-side movable body that is provided distally in the connection direction, and at least one proximal-side movable body that is provided proximally in the connection direction, and wherein an operation tolerance of the at least one distal-side movable body is higher than an operation tolerance of the at least one proximal-side movable body.

According to yet another aspect of one or more embodiments, there is provided a surgery-assisting device comprising a robot arm comprising a plurality of sections, each section being one of a joint section or an arm section, a first portion of the plurality of sections being located distally on the robot arm and a second portion of the plurality of sections being located proximally on the robot arm; a surgical instrument connected to a distal end of the robot arm; and at least one actuator that is configured to generate a driving force that operates at least one of the plurality of sections, wherein an operation tolerance of each of one or more sections included in the first portion is higher than an operation tolerance of each of one or more sections included in the second portion such that an external force operates the one or more sections included in the first portion more easily than the external force operates the one or more sections included in the second portion.

BRIEF DESCRIPTION OF DRAWINGS

The above and/or other aspects will become apparent and more readily, appreciated from the following description of exemplary embodiments, taken in conjunction with the accompanying drawings in which.

DETAILED DESCRIPTION

In recent years, surgical operations using surgery-assisting devices have come into widespread use. Such a surgery-assisting device includes a plurality of movable bodies that are operably connected to one another in order and actuators that generate driving forces for operating the movable bodies, and a movable body positioned at one end in a connecting direction is provided with a holding portion. The plurality of movable bodies are provided as an arm section and/or a joint section. The holding portion holds a surgical instrument that is partly inserted into the body cavity of a patient. As the surgical instrument, various types of instruments such as a type having an endoscope and a type having both forceps and an endoscope are used according to a kind of surgery and conditions.

When the plurality of movable bodies are each operated in a predetermined direction in the surgery-assisting device, the surgical instrument is moved along with the operation of the movable bodies, and the pose of the surgical instrument is also changed. Thus, a surgical operation is performed in a state in which a part (e.g., a distal end portion) of the surgical instrument is inserted in the body cavity of the patient.

The surgical operation using the surgery-assisting device as described above is generally performed by an operator (surgeon) who remotely operates the surgery-assisting device installed in an operating room according to a master-slave system. When such a surgical operation is performed, a pivot point is set to serve as a reference point for movement of the surgical instrument. The pivot point in the surgery-assisting device is roughly classified into a type in which a pivot point is mechanically fixed to a movable body and a type in which a pivot point is virtually set using/by control software.

The pivot point is a position substantially coinciding with a port which is formed in the body cavity of the patient and through which the surgical instrument is to be inserted. In a case where a trocar is used, the pivot point substantially coincides with the position of the trocar. Hence, in a state in which the surgical instrument is inserted in the body cavity of the patient, a position and pose of the surgical instrument are controlled such that a part of the surgical instrument passes through the pivot point at all times. When a part of the surgical instrument passes through the pivot point, the occurrence of a load on a tissue in the vicinity of the body surface of the patient is prevented, and thus, safety is ensured.

Meanwhile, in the surgical operation using the surgery-assisting device, it is important not only to enhance the safety of the surgery but also to enhance the accuracy of the surgery. In order to enhance the accuracy of the surgery, it is necessary to precisely control the position and pose of the movable bodies and to enhance positional accuracy at a distal end portion of the surgical instrument inserted in the body cavity.

However, whereas not only a surgeon and assistants but also many appliances and equipment for surgery are present in the operating room in which the surgical operation is performed, an area of the operating room is limited. Thus, it may not be possible to secure a sufficient arrangement space for the surgery-assisting device. Accordingly, there is a possibility that a person, an appliance, or the like present in the operating room may unexpectedly come into contact with the surgery-assisting device, a force of the contact may be applied as an external force to the movable bodies, and the position and pose of the movable bodies may be changed to disturb the position and pose of the surgical instrument.

Hence, in order to precisely control the position and pose of the movable bodies, the movable bodies need to be prevented from being displaced due to the external force when the force is unexpectedly applied from the outside to the movable bodies. Connecting parts between the movable bodies are thus desired to have a high stiffness. As means for ensuring the high stiffness at the connecting parts between such movable bodies and preventing the occurrence of a problem due to the external force, the movable bodies may be operated with the use of electric actuators that generate a driving force by a motor. When the electric actuators are used, the connecting parts between the movable bodies are held in a secure state by the holding forces of the electric actuators, thereby preventing displacement of the movable bodies when the force is unexpectedly applied from the outside to the movable bodies.

However, the surgical operation is, for example, often performed in a pneumoperitoneum state in Which an abdominal cavity is expanded by a carbonic acid gas or the like. A change in abdominal cavity pressure may cause a difference between a virtual pivot point set for the device and an actual pivot point in the port. When the connecting parts between the movable bodies have a high stiffness as described above in a case where such a difference has been caused, each movable body is operated in a state in which the set virtual pivot point is maintained. Thus, the surgical instrument may come into contact with a tissue in the vicinity of a body surface on the periphery of the port, and a heavy load caused by the contact may cause damage to the tissue or the like, so that safety may be impaired.

Accordingly, in order to prevent damage to the tissue or the like due to the difference between the virtual pivot point set on the control software and the actual pivot point in the port of the patient, a surgery-assisting device may measure torque acting on movable bodies with the use of torque sensors and operating the movable bodies according to measurement results of the torque sensors.

The surgery-assisting device that uses torque sensors is intended to prevent damage to the tissue due to a difference between a virtual pivot point and an actual pivot point in the port. However, the implementation of the torque sensors in the surgery-assisting device having such a configuration causes a rise in manufacturing cost and complicates operation control on each movable body.

Hence, not only is a rise in manufacturing cost caused, but also it may be difficult to sufficiently suppress the occurrence of the load on the tissue in the vicinity of the body surface on the periphery of the port due to the complication of the operation control on each movable body.

Accordingly, it is an aspect of a surgery-assisting device according to various embodiment to achieve an improvement in safety without causing a rise in manufacturing cost, and to achieve an improvement in positional accuracy at a distal end portion of a surgical instrument.

A surgery-assisting device according to some embodiments may include a plurality of movable bodies operably connected to one another in order, and at least one actuator configured to generate a driving force that operates at least one of the movable bodies. One of the plurality of movable bodies that is positioned at one end in a connecting direction may include a holding portion configured to hold a surgical instrument. At least one of the movable bodies that is positioned on a side of the surgical instrument in the connecting direction and that includes the movable body having the holding portion may be provided as a distal-side movable body, and at least one of the movable bodies that includes the movable body positioned farthest from the surgical instrument in the connecting direction and that is other than the distal-side movable body may be provided as a proximal-side movable body. When a degree of tolerance for operation of the movable body at a time when an external force other than the driving force of the actuator is applied to the movable body is operation tolerance, the operation tolerance of the distal-side movable body may be set higher than the operation tolerance of the proximal-side movable body.

Thus, when an external force other than the driving force of the actuator is applied to the movable bodies, the distal-side movable body positioned on the surgical instrument side may be operated more easily according to the external force than the proximal-side movable body positioned at a distance away from the surgical instrument.

In the surgery-assisting device according to some embodiments, the plurality of movable bodies may each have one degree of freedom in an operating direction, and six movable bodies may be provided to enable operation with six degrees of freedom.

Thus, an operation control performed on each movable body may be simplified, and there may be many degrees of freedom operating directions of the surgical instrument.

In the surgery-assisting device according to some embodiments, three proximal-side movable bodies and three distal-side movable bodies may be provided.

Thus, an excellent balance with regard to the operation tolerance of the movable bodies may be ensured.

In the surgery-assisting device according to some embodiments, the plurality of movable bodies may each have one degree of freedom in an operating direction, and seven movable bodies may be provided to enable operation with seven degrees of freedom.

Thus, an operation control performed on each movable body may be simplified, and there may be more degrees of freedom in operating directions of the surgical instrument.

In the surgery-assisting device according to some embodiments, at least one pneumatic actuator configured to generate a driving force by a change in pressure of a gas and at least one electric actuator configured to generate a driving force by a motor may be provided as the actuators, the proximal-side movable body may be operated by the electric actuator, and the distal-side movable body may be operated by the pneumatic actuator.

Thus, the movable body positioned at a distance away from the surgical instrument may be operated by the electric actuator, and the movable body positioned on a side close to the surgical instrument may be operated by the pneumatic actuator.

In the surgery-assisting device according to some embodiments, only the proximal-side movable body among the movable bodies may be operated by the actuator.

Thus, there may be adopted a configuration in which the driving of the proximal-side movable body is performed by the actuator, and the distal-side movable body has no driving source for operation.

According to the surgery-assisting device according to various embodiments, when an external force other than the driving force of the actuator is applied to the movable bodies, the distal-side movable body positioned on the surgical instrument side may be operated mote easily according to the external force than the proximal-side movable body positioned at a distance away from the surgical instrument. It is thus possible to achieve an improvement in safety without causing a rise in manufacturing cost, and to achieve an improvement in positional accuracy at a distal end portion of the surgical instrument.

A surgery-assisting device according to various embodiments will hereinafter be described with reference to the accompanying drawings.

The description herein represents an example in which the surgery-assisting device according to some embodiments is applied as a type used in a state of being installed on the floor of an operating room or the like. However, the scope of the embodiments of the present disclosure is not limited to the type used in a state of being installed on the floor of an operating room or the like, and some embodiments may be applied to a type used in a state of being attached to the ceiling or wall surface of an operating room.

It is to be noted that forward and rearward, upward and downward, and leftward and rightward directions illustrated in the following are directions chosen for the convenience of description and are not limited to these directions in carrying out the various embodiments.

In addition, the surgery-assisting device according to some embodiments has a configuration in which movable bodies are rotated. Here, "rotation" means operation in an axial rotation direction about a reference axis (central axis) including an optional point, and refers to operation including also "revolution." it is to be noted that, while an example in which the movable bodies are rotationally operated will be described, the operation of the movable bodies is not limited to rotational operation, and in some embodiments, a rectilinear operation of the movable bodies may be performed. The term "operation" includes both the rotational operation and the rectilinear operation.

<Configuration>

Figure 1:
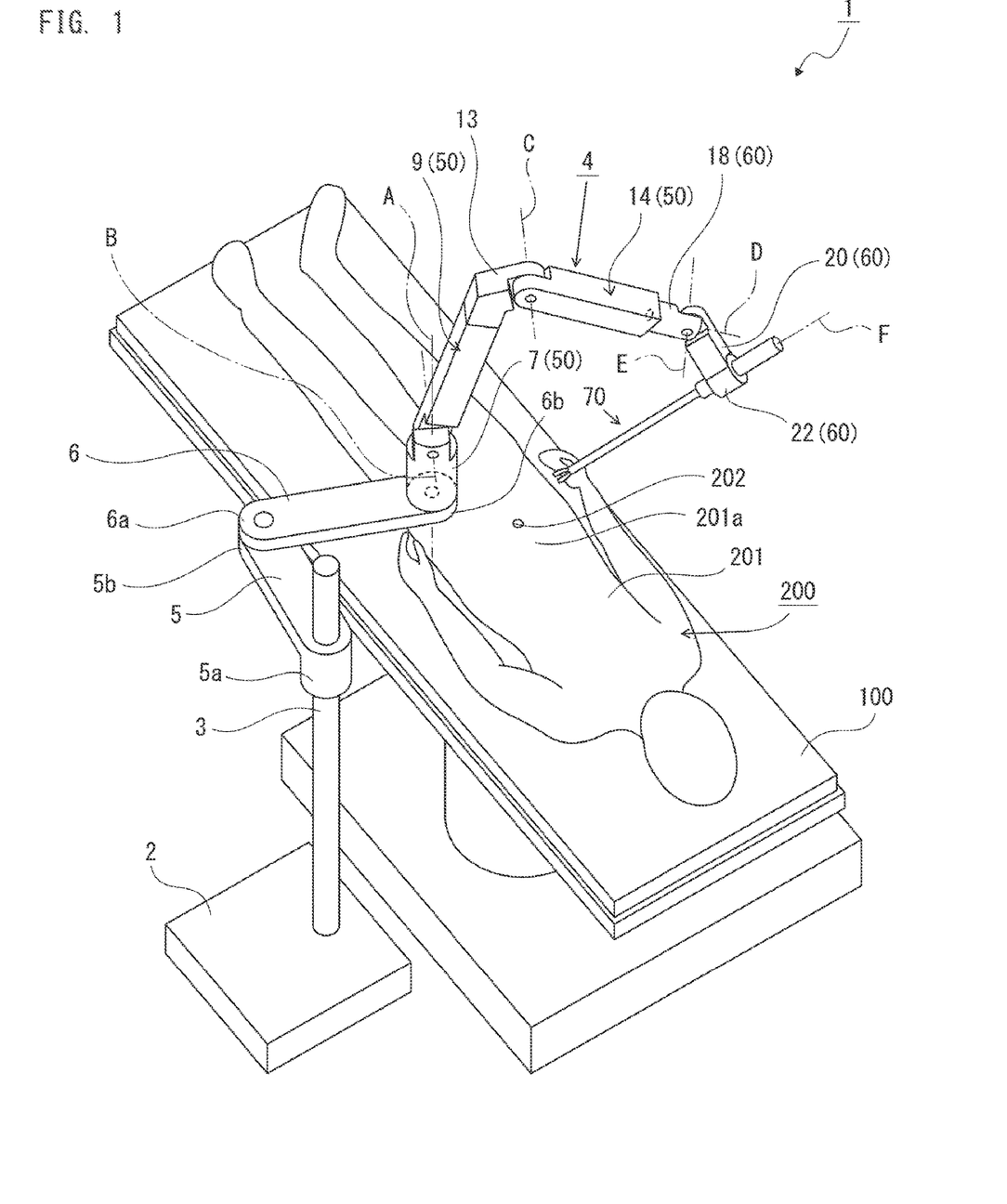
FIG. 1 depicts a schematic perspective view of a surgery-assisting device, according to various embodiments.
Figure 2:
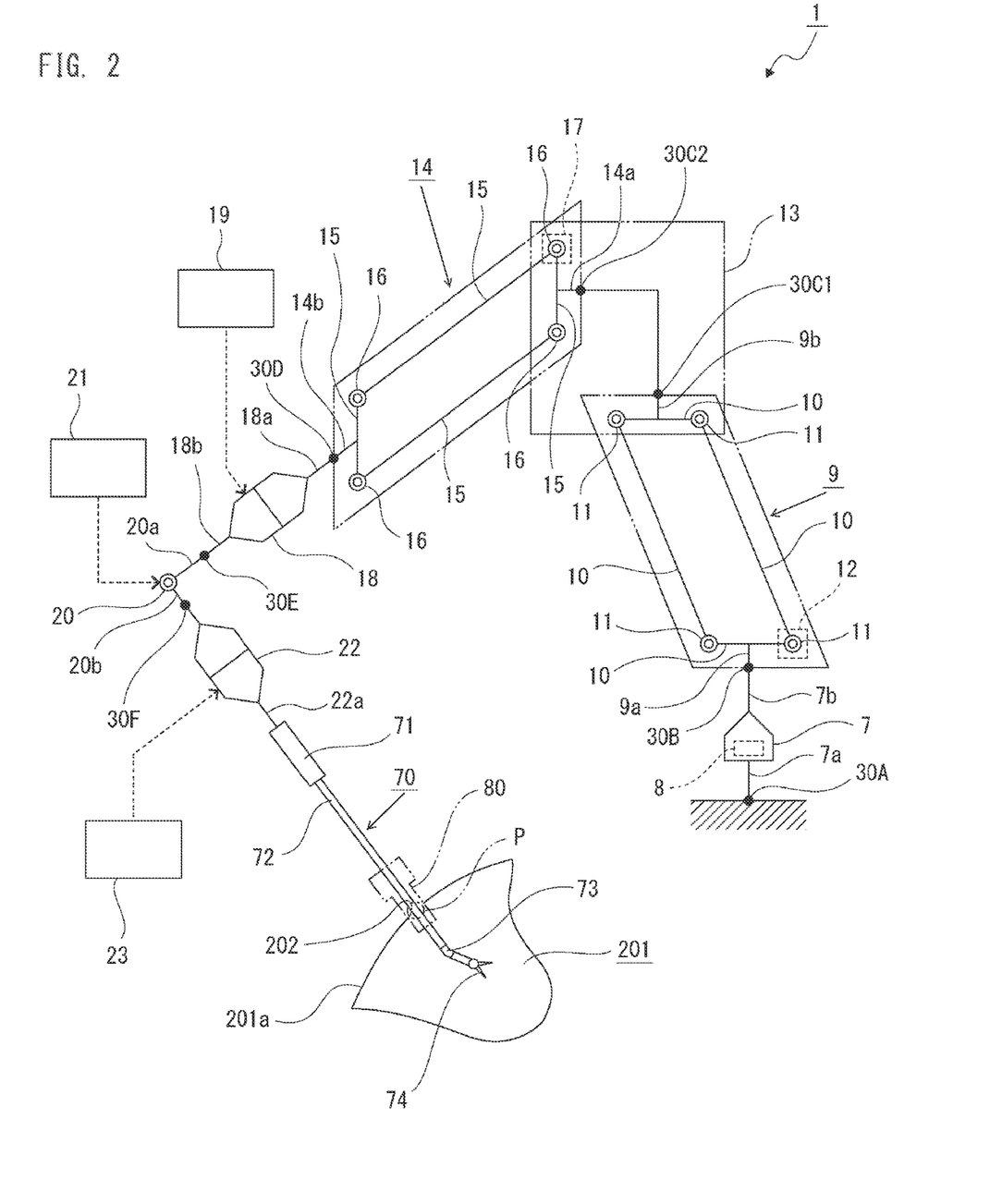
FIG. 2 is a conceptual diagram of the surgery-assisting device of FIG. according to some embodiments.
Figure 3:
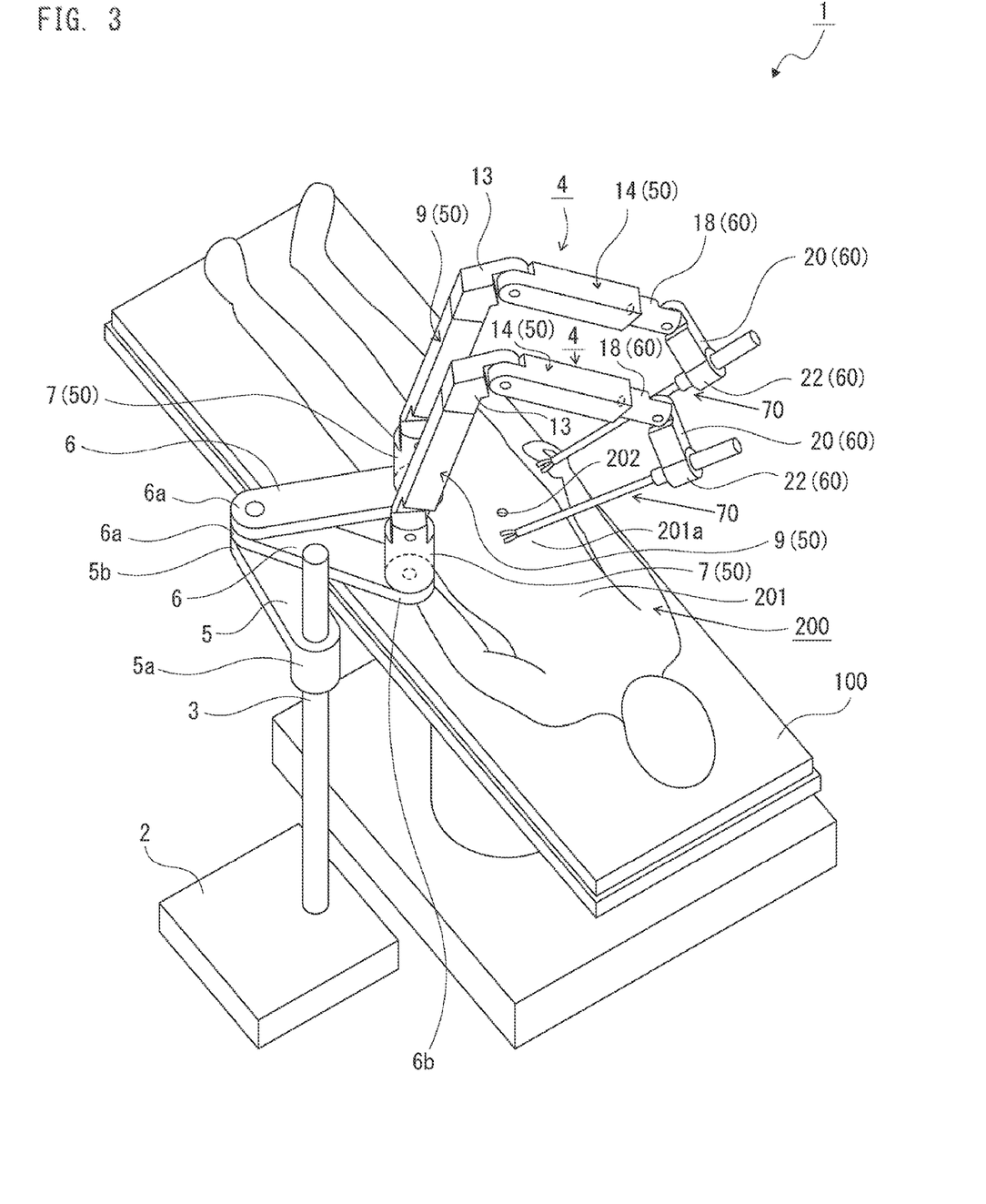
FIG. 3 is a schematic perspective view depicting a surgery-assisting device, according to some embodiments.

A configuration of a surgery-assisting device 1 will be described with respect to FIGS. 1 to 3, in which FIG. 1 depicts a schematic perspective view of a surgery-assisting device, according to various embodiments, FIG. 2 is a conceptual diagram of the surgery-assisting device of FIG. 1, according to some embodiments, and FIG. 3 is a schematic perspective view depicting a surgery-assisting device, according to some embodiments.

An operating table 100 may be installed in the operating room. A patient 200 is laid down on his or her back, for example, on the operating table 100 (see FIG. 1). A port 202 is formed in a body cavity 201, for example, in an abdominal wall 201a of the patient 200. A part (e.g., a distal end portion) of a surgical instrument to be described later is inserted into the port 202 when a surgical operation is performed. The port 202 is a small hole into which a shaft-shaped surgical instrument is inserted.

The surgery-assisting device 1 includes a base 2 placed on the floor of the operating room or the like, a pole 3 in a round shaft shape which pole is fixed to the base 2, and a main unit 4 supported by the pole 3. The base 2 is installed on the floor or the like on a side of the operating table 100. A lower end portion of the pole 3 is fixed to the base 2 in a state in which the pole 3 extends vertically.

The main unit 4 is supported by the pole 3 in such a manner as to be movable in an upward-downward direction. The main unit 4 has a configuration in which respective parts thereof are connected to one another in a rotatable state. The main unit 4 can be fixed to the pole 3 at a desired position in the upward-downward direction. In some embodiments, various parts of the main unit 4 may be controlled by the hardware control logic, at least one controller and/or at least one microprocessor that is communicatively coupled to the main unit 4.

The main unit 4 includes a first connecting arm 5 and a second connecting arm 6 rotatably connected to each other.

The first connecting arm 5 is formed in a shape extending in a horizontal direction. The first connecting arm 5 has a supported tubular portion 5a at one end portion thereof in a longitudinal direction and has a pivot portion 5b at the other end portion thereof in the longitudinal direction. The pole 3 is inserted through the supported tubular portion 5a of the first connecting arm 5. The first connecting arm 5 can manually or electrically be moved in the upward-downward direction with respect to the pole 3, and can be revolved in an axial rotation direction with respect to the pole 3 with the supported tubular portion 5a as a pivot.

The first connecting arm 5 can be fixed to the pole 3 at a desired position in the upward-downward direction and at a desired position in the axial rotation direction.

The second connecting arm 6 is formed in a shape extending in the horizontal direction. The second connecting arm 6 has a pivot portion 6a at one end portion thereof in a longitudinal direction and has a supporting shaft portion 6b at the other end portion thereof in the longitudinal direction. The pivot portion 6a of the second connecting arm 6 is vertically superposed on the pivot portion 5b of the first connecting arm 5. The pivot portion 6a of the second connecting arm 6 and the pivot portion 5b of the first connecting arm 5 are connected to each other in a rotatable state. The second connecting arm 6 can manually or electrically be rotated with respect to the first connecting arm 5 with the pivot portion 6a as a pivot.

The main unit 4 includes a first movable body 7 that functions as a joint section. The first movable body 7 is rotatably connected to the supporting shaft portion 6b of the second connecting arm 6 (see FIG. 1 and FIG. 2). The first movable body 7 has a proximal end side connecting portion 7a at an end portion thereof on the second connecting arm 6 side and has a distal end side connecting portion 7b at an end portion thereof on a side opposite to the second connecting arm 6 side. The proximal end side connecting portion 7a of the first movable body 7 is rotatably connected to the supporting shaft portion 6b of the second connecting arm 6. The first movable body 7 is, for example, rotated with respect to the second connecting arm 6 in an axial rotation direction about a reference axis A extending in the upward-downward direction. Hence, because the first movable body 7 is rotated with respect to the second connecting arm 6, the surgery-assisting device 1 has one degree of freedom in an operating direction.

A first electric actuator 8 that generates a driving force by a motor is disposed in the first movable body 7. In some embodiments, the first electric actuator 8 may be controlled by the hardware control logic, the at least one controller or the at least one microprocessor. The first movable body 7 is rotated with respect to the second connecting arm 6 by the driving force of the first electric actuator 8. Because the first movable body 7 is thus rotated by the driving force of the first electric actuator 8, a connecting part 30A between the first movable body 7 and the second connecting arm 6 is held in a secure state by the holding force of the first electric actuator 8, and thus has a high stiffness, in some embodiments, the first electric actuator 8 may be disposed in the second connecting arm 6.

The main unit 4 includes a second movable body 9 that functions as an arm section. The second movable body 9 is rotatably connected to the distal end side connecting portion 7b of the first movable body 7. The second movable body 9 has a proximal end side connecting portion 9a at one end portion thereof in a longitudinal direction and has a distal end side connecting portion 9b at the other end portion thereof in the longitudinal direction. The proximal end side connecting portion 9a of the second movable body 9 is rotatably connected to the distal end side connecting portion 7b of the first movable body 7. The second movable body 9 is, for example, rotated with respect to the first movable body 7 in an axial rotation direction about a reference axis B extending in a direction orthogonal to the connecting direction in which the second movable body 9 and the first movable body 7 are connected to each other. Hence, because the second movable body 9 is rotated with respect to the first movable body 7, the surgery-assisting device 1 has one degree of freedom in an operating direction.

The second movable body 9 is provided with a link mechanism, for example. The link mechanism includes two sets of parallel link portions 10 and coupling pins 11 that couple the link portions 10 to each other. In the second movable body 9, the coupling pins 11 positioned on the first movable body 7 side are connected in a rotatable state to the distal end side connecting portion 7b of the first movable body 7.

A second electric actuator 12 that generates a driving force by a motor is disposed in the second movable body 9. In some embodiments, the second electric actuator 12 may be controlled by the hardware control logic, the at least one controller or the at least one microprocessor. The second movable body 9 is rotated with respect to the first movable body 7 by the driving force of the second electric actuator 12. Because the second movable body 9 is thus rotated by the driving force of the second electric actuator 12, a connecting part 30B between the second movable body 9 and the first movable body 7 is held in a secure state by the holding force of the second electric actuator 12, and thus has a high stiffness. In some embodiments, the second electric actuator 12 may be disposed in the first movable body 7.

The distal end side connecting portion 9b of the second movable body 9 is connected to an intermediate connecting member 13. In the second movable body 9, the coupling pins 11 positioned on the intermediate connecting member 13 side are connected in a rotatable state to one end portion of the intermediate connecting member 13. Because the second movable body 9 is rotated by the driving force of the second electric actuator 12, a connecting part 30C1 between the second movable body 9 and the intermediate connecting member 13 is held in a secure state by the holding force of the second electric actuator 12, and thus has a high stiffness.

The main unit 4 includes a third movable body 14 that functions as an arm section. The third movable body 14 is connected to the intermediate connecting member 13. The third movable body 14 has a proximal end side connecting portion 14a at one end portion thereof in a longitudinal direction and has a distal end side connecting portion 14b at the other end portion thereof in the longitudinal direction. The proximal end side connecting portion 14a of the third movable body 14 is connected to the intermediate connecting member 13. The third movable body 14 is, for example, rotated with respect to the intermediate connecting member 13 in an axial rotation direction about a reference axis C extending in a direction orthogonal to the connecting direction in which the third movable body 14 and the intermediate connecting member 13 are connected to each other. Hence, because the third movable body 14 is rotated with respect to the intermediate connecting member 13, the surgery-assisting device 1 has one degree of freedom in an operating direction.

The third movable body 14 is provided with a link mechanism, for example. The link mechanism includes two sets of parallel link portions 15 and coupling pins 16 that couple the link portions 15 to each other. In the third movable body 14, the coupling pins 16 positioned on the intermediate connecting member 13 side are connected in a rotatable state to the other end portion of the intermediate connecting member 13.

While the above description illustrates an example in which the second movable body 9 and the third movable body 14 are connected to each other via the intermediate connecting member 13, the surgery-assisting device 1 according to some embodiments may omit the intermediate connecting member 13, and the second movable body 9 and the third movable body 14 may be connected to each other without the intervention of the intermediate connecting member 13. In a case where the second movable body 9 and the third movable body 14 are connected to each other without the intervention of the intermediate connecting member 13, the third movable body 14 is rotated with respect to the second movable body 9, and thus, the surgery-assisting device 1 according to some embodiments may have one degree of freedom in an operating direction.

A third electric actuator 17 that generates a driving force by a motor is disposed in the third movable body 14. In some embodiments, the third electric actuator 17 may be controlled by the hardware control logic, the at least one controller or the at least one microprocessor. The third movable body 14 is rotated with respect to the intermediate connecting member 13 by the driving force of the third electric actuator 17. Because the third movable body 14 is thus rotated by the driving force of the third electric actuator 17, a connecting part 30C2 between the third movable body 14 and the intermediate connecting member 13 is held in a secure state by the holding force of the third electric actuator 17, and thus has a high stiffness. In some embodiments, the third electric actuator 17 may be disposed in the intermediate connecting member 13.

The first movable body 7, the second movable body 9, and the third movable body 14 described above are all set as proximal-side movable bodies 50 located at a distance away from the surgical instrument in the connecting direction. As described above, the connecting parts 30A, 30B, 30C1, and 30C2 in the first movable body 7, the second movable body 9, and the third movable body 14 set as the proximal-side movable bodies 50 have a high stiffness.

The main unit 4 includes a fourth movable body 18 that functions as a joint section. The fourth movable body 18 is rotatably connected to the distal end side connecting portion 14b of the third movable body 14. The fourth movable body 18 has a proximal end side connecting portion 18a at an end portion thereof on the third movable body 14 side and has a distal end side connecting portion 18b at an end portion thereof on a side opposite to the third movable body 14 side. The proximal end side connecting portion 18a of the fourth movable body 18 is rotatably connected to the distal end side connecting portion 14b of the third movable body 14. The fourth movable body 18 is, for example, rotated with respect to the third movable body 14 in an axial rotation direction about a reference axis D extending in the connecting direction in which the fourth movable body 18 and the third movable body 14 are connected to each other. Hence, because the fourth movable body 18 is rotated with respect to the third movable body 14, the surgery-assisting device 1 according to some embodiments may have one degree of freedom in an operating direction.

The driving force of a first pneumatic actuator 19 is transmitted to the fourth movable body 18. In some embodiments, the first pneumatic actuator 19 may be controlled by the hardware control logic, the at least one controller or the at least one microprocessor. The first pneumatic actuator 19 generates the driving force by a change in the pressure of a gas such as air. The fourth movable body 18 is rotated with respect to the third movable body 14 by the driving force of the first pneumatic actuator 19. Because the fourth movable body 18 is thus rotated by the driving force of the first pneumatic actuator 19, a connecting part 30D between the fourth movable body 18 and the third movable body 14 is held by a holding force weaker than that of an electric actuator, and thus has a lower stiffness than the connecting parts 30A, 30B, 30C1, and 30C2 in the proximal-side movable bodies 50.

The main unit 4 includes a fifth movable body 20 that functions as a joint section. The fifth movable body 20 is rotatably connected to the distal end side connecting portion 18b of the fourth movable body 18. The fifth movable body 20 has a proximal end side connecting portion 20a at an end portion thereof on the fourth movable body 18 side and has a distal end side connecting portion 20b at an end portion thereof on a side opposite to the fourth movable body 18 side. The proximal end side connecting portion 20a of the fifth movable body 20 is rotatably connected to the distal end side connecting portion 18b of the fourth movable body 18. The fifth movable body 20 is, for example, rotated with respect to the fourth movable body 18 in an axial rotation direction about a reference axis E extending in a direction orthogonal to the connecting direction in which the fifth movable body 20 and the fourth movable body 18 are connected to each other. Hence, because the fifth movable body 20 is rotated with respect to the fourth movable body 18, the surgery-assisting device 1 has one degree of freedom in an operating direction.

The driving force of a second pneumatic actuator 21 is transmitted to the fifth movable body 20. In some embodiments, the second pneumatic actuator 21 may be controlled by the hardware control logic, the at least one controller or the at least one microprocessor. The second pneumatic actuator 21 generates the driving force by a change in the pressure of a gas such as air. The fifth movable body 20 is rotated with respect to the fourth movable body 18 by the driving force of the second pneumatic actuator 21. Because the fifth movable body 20 is thus rotated by the driving force of the second pneumatic actuator 21, a connecting part 30E between the fifth movable body 20 and the fourth movable body 18 is held by a holding force weaker than that of an electric actuator, and thus has a lower stiffness than the connecting parts 30A, 30B, 30C1, and 30C2 in the proximal-side provable bodies 50.

The main unit 4 includes a sixth movable body 22. The sixth movable body 22 is rotatably connected to the distal end side connecting portion 20b of the fifth movable body 20. The sixth movable body 22 is formed in a substantially cylindrical shape, for example. At least a part of the sixth movable body 22 is provided as a holding portion 22a. The sixth movable body 22 is rotatably connected to the distal end side connecting portion 20b of the fifth movable body 20. The sixth movable body 22 is, for example, rotated with respect to the fifth movable body 20 in an axial rotation direction about a reference axis F extending in an axial direction. Hence, because the sixth movable body 22 is rotated with respect to the fifth movable body 20, the surgery-assisting device 1 according to some embodiments may have one degree of freedom in an operating direction.

The driving force of a third pneumatic actuator 23 is transmitted to the sixth movable body 22. In some embodiments, the third pneumatic actuator 23 may be controlled by the hardware control logic, the at least one controller or the at least one microprocessor. The third pneumatic actuator 23 generates the driving force by a change in the pressure of a gas such as air. The sixth movable body 22 is rotated with respect to the fifth movable body 20 by the driving force of the third pneumatic actuator 23. Because the sixth movable body 22 is thus rotated by the driving force of the third pneumatic actuator 23, a connecting part 30F between the sixth movable body 22 and the fifth movable body 20 is held by a holding force weaker than that of an electric actuator, and thus has a lower stiffness than the connecting parts 30A, 30B, 30C1, and 30C2 in the proximal-side movable bodies 50.

The fourth movable body 18, the fifth movable body 20, and the sixth movable body 22 described above are all set as distal-side movable bodies 60 positioned on the surgical instrument side in the connecting direction. As described above, the connecting parts 30D, 30E, and 30F in the fourth movable body 18, the fifth movable body 20, and the sixth movable body 22 set as the distal-side movable bodies 60 have a lower stiffness than the connecting parts 30A, 30B, 30C1, and 30C2 in the first movable body 7, the second movable body 9, and the third movable body 14 set as the proximal-side movable bodies 50.

The holding portion 22a of the sixth movable body 22 holds a surgical instrument 70. The surgical instrument 70 is, for example, formed in a shaft shape as a whole. The surgical instrument 70 includes a held section 71 held by the holding portion 22a, a shaft section 72 projecting from the held section 71, a bent section 73 disposed in such a manner as to be continuous with a distal end of the shaft section 72, and an operating section 74 such as forceps disposed in such a manner as to be continuous with the bent section 73.

The surgical instrument 70 may be held by the holding portion 22a in a state in which the surgical instrument 70 is movable in the axial direction of the shaft section 72.

A distal end portion of the shaft section 72 which distal end portion includes at least the bent section 73 and the operating section 74 is inserted into the port 202 formed in the body cavity 201 of the patient 200. In addition, in a case where a trocar 80 is used in the surgical operation, a part of the shaft section 72 on the distal end side thereof is inserted into the port 202 through the trocar 80.

The bent section 73 can be bent with respect to the axial direction of the shaft section 72. The pose of the operating section 74 is changed when the bent section 73 is bent with respect to the shaft section 72.

It is to be noted that, while the above description illustrates, as an example, the surgery-assisting device 1 according to some embodiments which includes one main unit 4 having a plurality of movable bodies, in other embodiments, the number of main units 4 included in the surgery-assisting device 1 is not limited to one and may be plural (see FIG. 3). In a case where two main units 4, for example, are provided in such a surgery-assisting device 1, there may be adopted a configuration in which two second connecting arms 6 each rotatable with respect to the first connecting arm 5 are provided, and first movable bodies 7 are connected to the respective second connecting arms 6.

Thus, providing a plurality of main units 4 in such a manner enables a surgical operation to be performed with a plurality of surgical instruments 70 and thus enables a surgery time to be shortened. Also, it is possible to perform an advanced surgical operation by using a plurality of surgical instruments 70 of different kinds.

<Operation>

Figure 4:
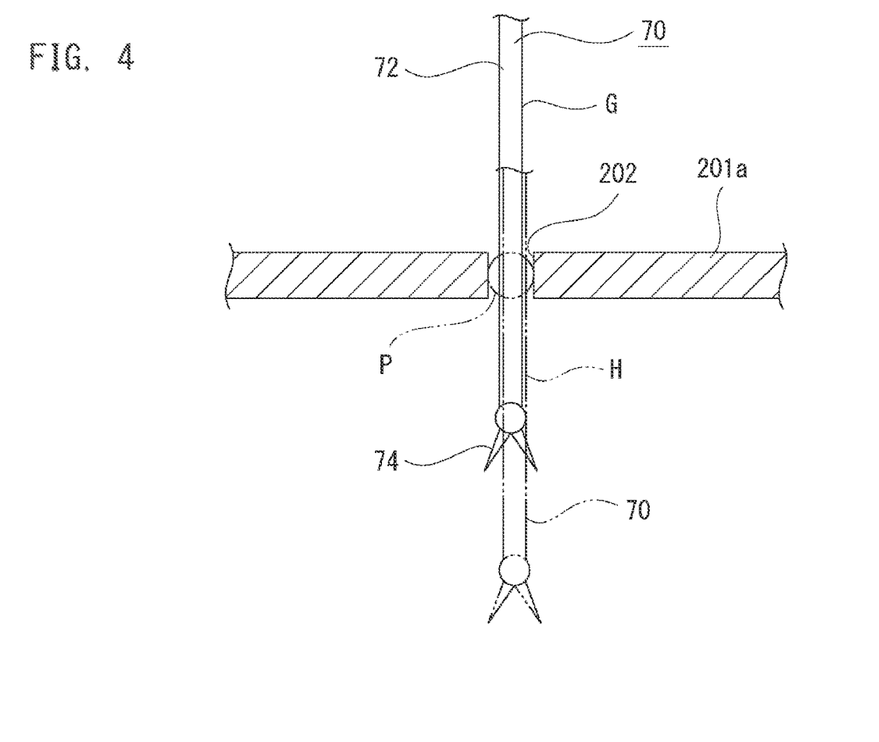
FIG. 4 is a conceptual diagram depicting a state in which a position of a surgical instrument is changed, according to some embodiments.
Figure 5:
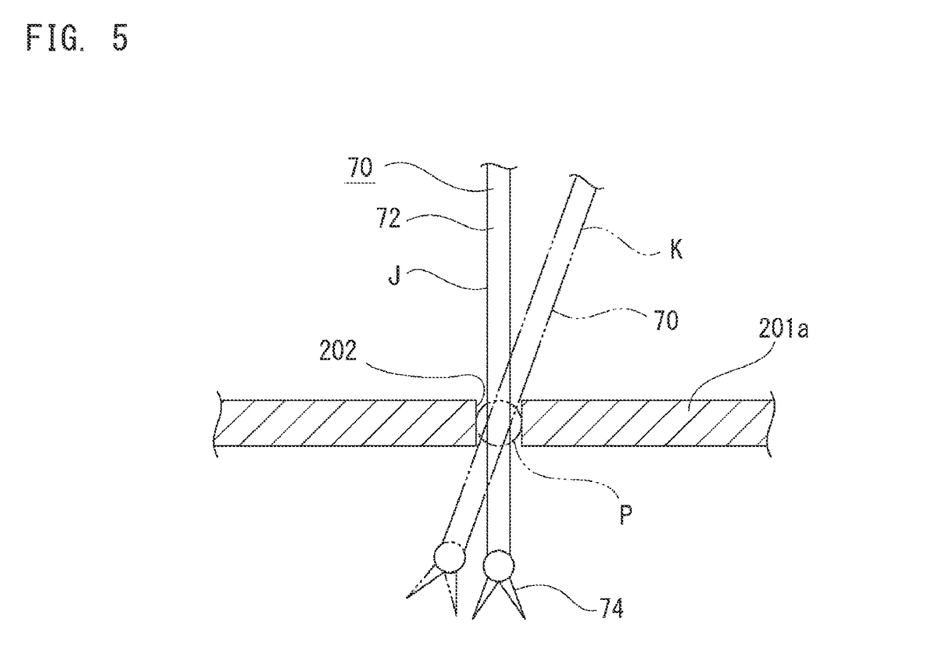
FIG. 5 is a conceptual diagram depicting a state in which a pose of the surgical instrument is changed, according to some embodiments.
Figure 6:
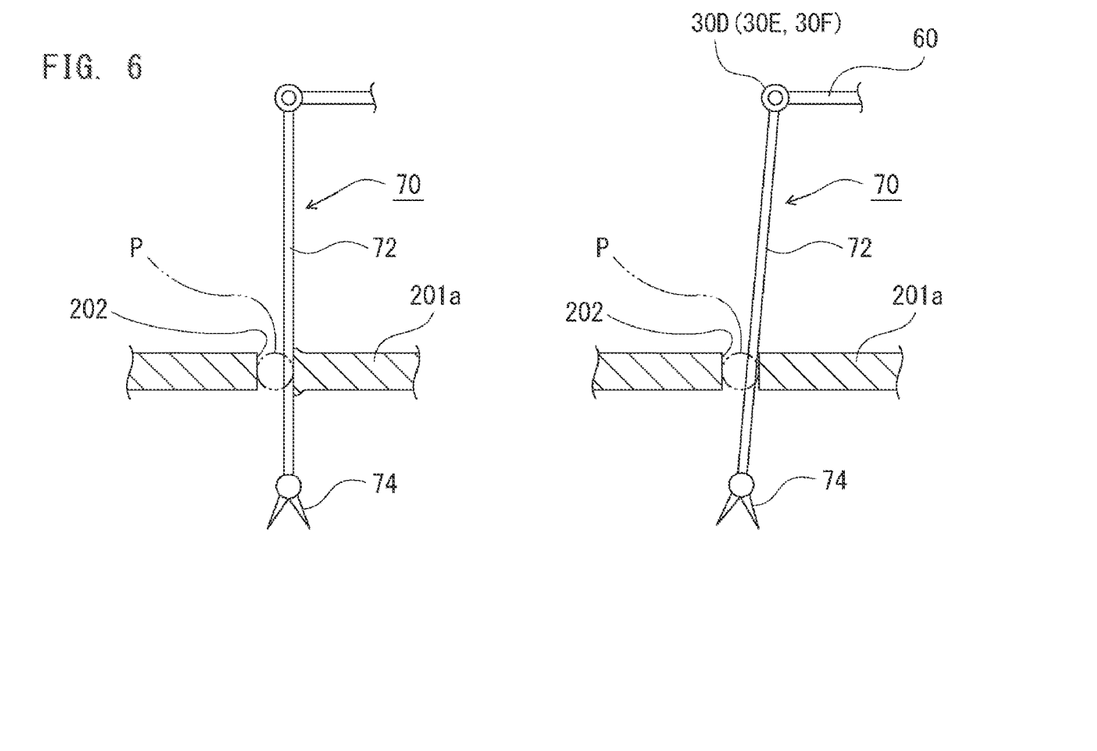
FIG. 6 depicts a state in which the position of the surgical instrument is shifted relative to a pivot point when the surgical instrument is inserted in a state of being perpendicular to a port, according to some embodiments.
Figure 7:
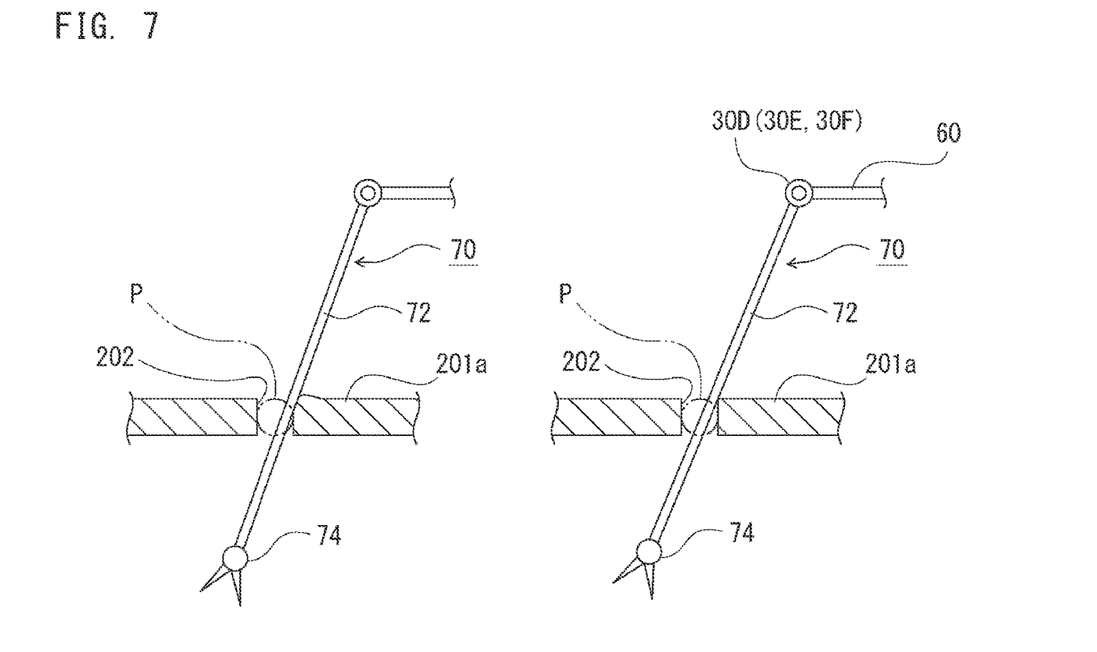
FIG. 7 depicts a state in which the position of the surgical instrument is shifted relative to the pivot point when the surgical instrument is inserted in a state of being inclined with respect to the port, according to some embodiments.

Operation of the surgery-assisting device 1 will next be described with reference to FIGS. 4 to 7. FIG. 4 is a conceptual diagram depicting a state in which a position of a surgical instrument is changed, according to one embodiments. FIG. 5 is a conceptual diagram depicting a state in which a pose of the surgical instrument is changed, according to some embodiments. FIG. 6 depicts a state in which the position of the surgical instrument is shifted relative to a pivot point when the surgical instrument is inserted in a state of being perpendicular to a port, according to some embodiments, and FIG. 7 depicts a state in which the position of the surgical instrument is shifted relative to the pivot point when the surgical instrument is inserted in a state of being inclined with respect to the port, according to some embodiments In the surgery-assisting device 1 configured as described with reference to FIGS. 1-3, when a surgical operation is performed, the first movable body 7, the second movable body 9, the third movable body 14, the fourth movable body 18, the fifth movable body 20, and the sixth movable body 22 are rotationally operated such that the position and pose of the surgical instrument 70 held by the holding portion 22a is changed to a desired state. In some embodiments, in the surgery-assisting device 1 the first movable body 7, the second movable body 9, the third movable body 14, the fourth movable body 18, the fifth movable body 20, and the sixth movable body 22 may rectilinearly be operated such that the position and pose of the surgical instrument 70 held by the holding portion 22a is changed to a desired state.

In some embodiments, when the first movable body 7 is rotated, the second movable body 9, the third movable body 14, the fourth movable body 18, the fifth movable body 20, and the sixth movable body 22 are operated along with the rotational operation of the first movable body 7, to change the position or pose of the surgical instrument 70, When the second movable body 9 is rotated, the third movable body 14, the fourth movable body 18, the fifth movable body 20, and the sixth movable body 22 are operated along with the rotational operation of the second movable body 9, to change the position or pose of the surgical instrument 70. When the third movable body 14 is rotated, the fourth movable body 18, the fifth movable body 20, and the sixth movable body 22 are operated along with the rotational operation of the third movable body 14, to change the position or pose of the surgical instrument 70. When the fourth movable body 18 is rotated, the fifth movable body 20 and the sixth movable body 22 are operated along with the rotational operation of the fourth movable body 18, to change the position or pose of the surgical instrument 70. When the fifth movable body 20 is rotated, the sixth movable body 22 is operated along with the rotational operation of the fifth movable body 20, to change the position or pose of the surgical instrument 70. When the sixth movable body 22 is rotated, the surgical instrument 70 is rotated along with the rotational operation of the sixth movable body 22. In other words, when a movable body is rotated, downstream movable bodies are affected.

The surgical operation is, for example, performed by an operator (surgeon) who remotely operates the surgery-assisting device 1 installed in the operating room according to a master-slave system. The master-slave system is a system in which, when a plurality of devices are operated in cooperation with each other, roles are divided for a master machine in charge of control and operation of the plurality of devices and a slave machine operated under the control of the master machine. In this surgical operation, an operating device (control device) not depicted which device is operated by the operator is the master machine, and the surgery-assisting device 1 is the slave machine.

When the surgery-assisting device 1 is to be used in the surgical operation, first, the position of the main unit 4 in the upward-downward direction is set by moving the first connecting arm 5 in the upward-downward direction with respect to the pole 3 according to the position of the patient 200. Next, the position of the surgical instrument 70 is set by rotating the first connecting arm 5 with respect to the pole 3 and rotating the second connecting arm 6 with respect to the first connecting arm 5 according to a surgical operation position.

When the surgical operation is performed, a pivot point P which is a reference point for movement of the surgical instrument 70 is set (see FIG. 2, FIG. 4 and FIG. 5).

The pivot point P is a position substantially coinciding with the port 202 through which the surgical instrument 70 is to be inserted. In a case where the trocar 80 is used (see FIG. 2), the pivot point P substantially coincides with the position of the trocar 80. Hence, in a state in which the surgical instrument 70 is inserted in the body cavity 201 of the patient 200, if the position of the surgical instrument 70 is controlled and appropriate pivot operation is performed such that a part of the surgical instrument 70 passes through the pivot point P at all times, the occurrence of a load on a tissue in the vicinity of the body surface of the patient 200 is prevented even when the position of the surgical instrument 70 is changed (to position H in FIG. 4) from an original position (position G in FIG. 4). Thus, safety is ensured.

Incidentally, in FIG. 4, in order to facilitate understanding, the surgical instrument 70 moved in the axial direction of the shaft section 72 is illustrated such that the surgical instrument 70 which is yet to be moved and the surgical instrument 70 which has been moved are intentionally shifted from each other slightly in a direction orthogonal to the axial direction, and a solid line representing the surgical instrument 70 at the position G and a broken line representing the surgical instrument 70 at the position H do not coincide with each other.

In a state in which the surgical instrument 70 is inserted in the body cavity 201 of the patient 200, if the pose of the surgical instrument 70 is controlled and appropriate pivot operation is performed such that a part of the surgical instrument 70 passes through the pivot point P at all times, the occurrence of a load on a tissue in the vicinity of the body surface of the patient 200 is prevented even when the pose of the surgical instrument 70 is changed (to pose K in FIG. 5) from an original pose (pose in FIG. 5). Thus, safety is ensured.

In the surgical operation, there are a surgeon, assistants, and many appliances, equipment, instruments, etc. for surgery in the operating room. Therefore, particularly in a case where the area of the operating room is limited, there is a possibility that a person, an appliance, or the like present in the operating room may unexpectedly come into contact with parts of the surgery-assisting device 1, a force of the contact may be applied as an external force to the movable bodies to change the position and pose of the movable bodies, and the position and pose of the surgical instrument 70 may be disturbed due to the change in the position and pose of the movable bodies.

In addition, in a case where the surgical operation is performed in a pneumoperitoneum state in which an abdominal cavity is expanded by a carbonic acid gas or the like, a change in abdominal cavity pressure may possibly cause a difference between a virtual pivot point set in/by control software and an actual pivot point P in the port 202. Further, such an error (i.e., the difference) may be caused by a change in a heartbeat state or respiration of the patient 200.

When a force is thus externally applied to the movable bodies or the like or an error in the pivot point occurs, each movable body is operated in a state in which the virtual pivot point is maintained, and therefore, the position of the surgical instrument 70 is shifted relative to the actual pivot point Y. In a case where the connecting parts 30 between the movable bodies have a high stiffness, each movable body does not rotate easily, and the position of the surgical instrument 70 with respect to each movable body does not change easily. Thus, a part of the surgical instrument 70 or a part of the trocar 80 may be pressed against the opening edge of the port 202 in the body cavity 201 (see a diagram on the left side of FIG. 6 and a diagram on the left side of FIG. 7), and a heavy load may be applied to a tissue in the vicinity of the body surface on the periphery of the port 202 and cause damage to the tissue or the like, so that safety may be impaired.

However, in the surgery-assisting device 1 according to some embodiments, the respective connecting parts 30D, 30E, and 30F in the fourth movable body 18, the fifth movable body 20, and the sixth movable body 22 provided as the distal-side movable bodies 60 have a lower stiffness than the respective connecting parts 30A, 30B, 30C1, and 30C2 in the first movable body 7, the second movable body 9, and the third movable body 14 provided as the proximal-side movable bodies 50.

Hence, supposing that a degree of tolerance for rotation of a movable body at a time when external force other than the driving forces of the first electric actuator 8, the second electric actuator 12, the third electric actuator 17, the first pneumatic actuator 19, the second pneumatic actuator 21, and the third pneumatic actuator 23 is applied to the movable body is an operation tolerance (e.g., a rotation tolerance and/or a rectilinear tolerance), the operation tolerance (e.g., the rotation tolerance and/or the rectilinear tolerance) of the distal-side movable bodies 60 is set higher than the operation tolerance (e.g., the rotation tolerance and/or the rectilinear tolerance) of the proximal-side movable bodies 50. That is, when an external force other than the driving forces is applied to parts of the surgery-assisting device 1, the fourth movable body 18, the fifth movable body 20, and the sixth movable body 22 provided as the distal-side movable bodies 60 rotate more easily than the first movable body 7, the second movable body 9, and the third movable body 14 provided as the proximal-side movable bodies 50. In some embodiments, the operation tolerance may be set by the hardware control logic, the at least one controller, or the at least one microprocessor that is communicatively coupled to the main unit 4 and to the first electric actuator 8, the second electric actuator 12, the third electric actuator 17, the first pneumatic actuator 19, the second pneumatic actuator 21, and the third pneumatic actuator 23. For example, in some embodiments, the hardware control logic, the at least one controller, or the at least one microprocessor may control one or more of the first electric actuator 8, the second electric actuator 12, the third electric actuator 17, the first pneumatic actuator 19, the second pneumatic actuator 21, and the third pneumatic actuator 23 to set the force sense presenting function of the actuator.

Thus, in the surgery-assisting device 1 according to some embodiments, the distal-side movable bodies 60 rotate more easily than the proximal-side movable bodies 50. Therefore, when a force is externally applied to the movable bodies or the like or an error in the pivot point occurs, and when a part of the surgical instrument 70 or a part of the trocar 80 then comes into contact with the opening edge of the port 202, the fourth movable body 18, the fifth movable body 20, and the sixth movable body 22 are in a rotatable state (see a diagram on the right side of FIG. 6 and a diagram on the right side of FIG. 7).

Hence, when a part of the surgical instrument 70 or a part of the trocar 80 comes into contact with the opening edge of the port 202, at least one of the distal-side movable bodies 60 is rotated in response to the contact, and the surgical instrument 70 is displaced. Consequently, no heavy load is applied from the surgical instrument 70 to a tissue in the vicinity of the body surface on the periphery of the port 202, and damage to the tissue in the vicinity of the body surface or the like does not occur easily.

As described above, in the surgery-assisting device 1 according to some embodiments, at least one movable body that is positioned on the surgical instrument 70 side in the connecting direction in which the movable bodies are connected to each other and that includes the sixth movable body 22 having the holding portion 22a is provided as a distal-side movable body 60. At least one movable body that includes the first movable body 7 positioned farthest from the surgical instrument 70 in the connecting direction and that is other than the distal-side movable body 60 is provided as a proximal-side movable body 50. And the operation tolerance (e.g., the rotation tolerance and/or the rectilinear tolerance) of the distal-side movable body 60 is set higher than the operation tolerance (e.g., the rotation tolerance and/or the rectilinear tolerance) of the proximal-side movable body 50.

Hence, when an external force other than the driving forces of the actuators is applied to the movable bodies and the surgical instrument 70, the distal-side movable body 60 positioned on a side close to the surgical instrument 70 rotates more easily according to the external force than the proximal-side movable body 50 positioned at a distance away from the surgical instrument 70. Consequently, another part such as a torque sensor does not need to be used to ensure an improvement in safety, an improvement in safety can thus be achieved without causing a rise in manufacturing cost, and an improvement in positional accuracy at a distal end portion of the surgical instrument 70 can be achieved.

In addition, because of the high operation tolerance (e.g., the rotation tolerance and/or the rectilinear tolerance) of the distal-side movable body 60, when the surgical instrument 70 comes into contact with parts of the patient 200, the surgical instrument 70 can be made to respond sensitively to the contact state as a reaction, so that the contact between the movable body and the patient 200 at a time of the surgery is sensed easily. Thus, the surgery-assisting device 1 according to some embodiments is easily configured to ensure a force sense presenting function, and an improvement in accuracy of the surgery and an improvement in safety thereof can be achieved.

Further, in the surgery-assisting device 1 according to some embodiments, a plurality of movable bodies may each have one degree of freedom in an operating direction, and operation with six degrees of freedom may be enabled by providing six movable bodies.

Hence, operation control performed on each movable body is simplified, and there are many degrees of freedom in operating directions of the surgical instrument 70. It is thus possible to expand the operating range of the surgical instrument 70 and improve the positional accuracy of the surgical instrument 70 in addition to simplifying operation control on the movable bodies.

In some embodiments, because operation with six degrees of freedom is enabled by the six movable bodies, movement in three orthogonal axial directions of the surgical instrument 70 and a change in the pose thereof to an inclined state with respect to the three axial directions are performed. The surgical instrument 70 can thus be used in a desired position and a desired orientation with respect to the patient 200, so that a further improvement in accuracy of the surgery and a further improvement in safety thereof can be achieved.

That is, because movement in the three orthogonal axial directions of the surgical instrument 70 and a change in the pose thereof to an inclined state with respect to the three axial directions can be performed, the surgical instrument 70 can be held in a desired pose at any position in a space.

Further, a plurality of pneumatic actuators that generate a driving force by a change in pressure of a gas and a plurality of electric actuators that generate a driving force by a motor are provided as actuators, the proximal-side movable body 50 may be operated by an electric actuator, and the distal-side movable body 60 may be operated by a pneumatic actuator.

Hence, the movable body positioned at a distance away from the surgical instrument 70 is rotated by the electric actuator, and the movable body positioned on the side close to the surgical instrument 70 is rotated by the pneumatic actuator. Thus, stability of rotational positions of the movable bodies can be achieved, and operation tolerance (e.g., the rotation tolerance and/or the rectilinear tolerance) of the movable bodies at a time when an external force is applied to the movable bodies is increased, so that an improvement in safe can be achieved.

Because the movable body positioned on the side close to the surgical instrument 70 is rotated by the pneumatic actuator that implements a force sense presenting function easily, contact between the movable body and the body cavity 201 of the patient 200 at the time of the surgery is sensed easily, so that improvements in accuracy and safety of the surgery can be achieved.

<Modifications of Movable Bodies>

Various modifications of the movable bodies according to some embodiments will be described.

The above description illustrates example embodiments in which the surgery-assisting device 1 includes six movable bodies, that is, the first movable body 7, the second movable body 9, the third movable body 14, the fourth movable body 18, the fifth movable body 20, and the sixth movable body 22; the first movable body 7, the second movable body 9, and the third movable body 14 are each provided as a proximal-side movable body 50; and the fourth movable body 18, the fifth movable body 20, and the sixth movable body 22 are each provided as a distal-side movable body 60. However, embodiments are not limited thereto and, in some, embodiments, it suffices to provide at least one proximal-side movable body 50 and at least one distal-side movable body 60 in the surgery-assisting device 1.

That is, in some embodiments, as a proximal-side movable body 50, the first movable body 7 positioned farthest from the surgical instrument 70 in the connecting direction of the movable bodies may be provided, and as a distal-side movable body 60, the sixth movable body 22 positioned closest to the surgical instrument 70 in the connecting direction of the movable bodies may be provided. As for other movable bodies, any configuration can be adopted as long as movable bodies located on a side at a distance away from the surgical instrument 70 are provided as proximal-side movable bodies 50, and movable bodies located on the surgical instrument 70 side are provided as distal-side movable bodies 60.

For example, in some embodiments, only the first movable body 7 may be provided as a proximal-side movable body 50, and the second movable body 9, the third movable body 14, the fourth movable body 18, the fifth movable body 20, and the sixth movable body 22 may be provided as distal-side movable bodies 60. In other embodiments, the first movable body 7 and the second movable body 9 may be provided as proximal-side movable bodies 50, and the third movable body 14, the fourth movable body 18, the fifth movable body 20, and the sixth movable body 22 may be provided as distal-side movable bodies 60. In still other embodiments, the first movable body 7, the second movable body 9, the third movable body 14, and the fourth movable body 18 may be provided as proximal-side movable bodies 50, and the fifth movable body 20 and the sixth movable body 22 may be provided as distal-side movable bodies 60. In yet other embodiments, the first movable body 7, the second movable body 9, the third movable body 14, the fourth movable body 18, and the fifth movable body 20 may be provided as proximal-side movable bodies 50, and only the sixth movable body 22 may be provided as a distal-side movable body 60.

It is to be noted that, in a case where the surgery-assisting device 1 according to some embodiments is provided with three proximal-side movable bodies 50 and three distal-side movable bodies 60 as described above, the distal-side movable bodies 60 having a high operation tolerance (e.g., the rotation tolerance and/or the rectilinear tolerance) at a time when an external force other than the driving forces is applied to the movable bodies and the proximal-side movable bodies 50 having a low operation tolerance (e.g., the rotation tolerance and/or the rectilinear tolerance) at a time when the external force is applied to the movable bodies are provided in the same number in the configuration having six degrees of freedom.

Hence, an excellent balance with regard to the operation tolerance (e.g., the rotation tolerance and/or the rectilinear tolerance) of the movable bodies is ensured, and an improvement in the positional accuracy of the surgical instrument 70 and an improvement in safety at the time of the surgery can be achieved in addition to ensuring a wide operating range of the surgical instrument 70.

When the surgery-assisting device 1 according to some embodiments is provided with the three proximal-side movable bodies 50 and the three distal-side movable bodies 60, positional movement in the three orthogonal axial directions of the surgical instrument 70 is enabled by the three proximal-side movable bodies 50, and positional movement in the three orthogonal axial directions of the surgical instrument 70 is enabled also by the three distal-side movable bodies 60. Thus, an improvement in safety at the time of the surgery can be achieved by the three distal-side movable bodies 60 in addition to performing high-accuracy positioning with regard to the position and pose of the surgical instrument 70 by the three proximal-side movable bodies 50.

<Modifications of Actuators>

Modifications of the actuators will next be described.

The above description illustrates example embodiments in which the first movable body 7, the second movable body 9, and the third movable body 14 are each rotated by the driving force of an electric actuator, and the fourth movable body 18, the fifth movable body 20, and the sixth movable body 22 are each rotated by the driving force of a pneumatic actuator. However, embodiments are not limited thereto and, in some embodiments, actuators other than the electric actuators and the pneumatic actuators, such as hydraulic actuators, can be used as the driving sources of these movable bodies.

In the surgery-assisting device 1 according to some embodiments, with regard to the driving of the proximal-side movable bodies 50 and the distal-side movable bodies 60, in some embodiments, a configuration may be adopted in which the driving of the proximal-side movable bodies 50 is performed by electric actuators, and the driving of the distal-side movable bodies 60 is performed by hydraulic actuators, or in other embodiments, a configuration may be adopted in which the driving of the proximal-side movable bodies 50 is performed by hydraulic actuators, and the driving of the distal-side movable bodies 60 is performed by pneumatic actuators.

In either of the configurations, an improvement in the positional accuracy of the surgical instrument 70 and an improvement in safety at the time of the surgery can be achieved by making the operation tolerance (e.g., the rotation tolerance and/or the rectilinear tolerance) of the distal-side movable bodies 60 higher than the operation tolerance (e.g., the rotation tolerance and/or the rectilinear tolerance) of the proximal-side movable bodies 50.

However, in order to achieve stabilization and higher accuracy of a positioned state of the surgical instrument 70, the driving of the proximal-side movable bodies 50 in some embodiments may be performed by electric actuators that easily increase the stiffness of the connecting parts 30 provided between the movable bodies most.

In the surgery-assisting device 1 according to some embodiments, a configuration can be adopted in which the driving of the proximal-side movable bodies 50 is performed by either electric actuators, hydraulic actuators, or pneumatic actuators, and the distal-side movable bodies 60 have no driving source for rotational operation. In this case, rotational states of the distal-side movable bodies 60 may be maintained by frictional forces in the connecting parts 30.

Hence, because the proximal-side movable bodies 50 are driven by either electric actuators, hydraulic actuators, or pneumatic actuators, the proximal-side movable bodies 50 are set in an actively driven state. On the other hand, because the distal-side movable bodies 60 have no driving source, the distal-side movable bodies 60 are set in a passively driven state and are changed in position and pose along with movable operation of the proximal-side movable bodies 50.

In a case of such a configuration in which the driving of the proximal-side movable bodies 50 is performed by either electric actuators, hydraulic actuators, or pneumatic actuators, and the distal-side movable bodies 60 have no driving source for rotational operation, the movable body positioned at a distance away from the surgical instrument 70 is rotated by an electric actuator, and no driving force is applied to the movable body positioned on the side close to the surgical instrument 70.

Hence, the operation tolerance (e.g., the rotation tolerance and/or the rectilinear tolerance) of the distal-side movable bodies 60 is significantly higher than the operation tolerance (e.g., the rotation tolerance and/or the rectilinear tolerance) of the proximal-side movable bodies 50. It is thus possible to achieve stability of the rotational position of the movable bodies, and achieve an improvement in safety because of the high operation tolerance (e.g., the rotation tolerance and/or the rectilinear tolerance) of the movable bodies at a time when an external three is applied to the movable bodies.

When the configuration in which the distal-side movable bodies 60 have no driving source for rotational operation is adopted, the operation tolerance (e.g., the rotation tolerance and/or the rectilinear tolerance) of the distal-side movable bodies 60 can be made higher than that in the case where the driving of the distal-side movable bodies 60 is performed by pneumatic actuators. A further improvement in safety at the time of the surgery can thus be achieved.

As a kind of surgical instrument 70, there is a type having only a function of imaging the inside of the body cavity 201. In a case where a surgical instrument 70 having such a function is used in surgery, strict positional accuracy may not be needed as compared with the surgical instrument 70 having forceps or the like.

Hence, it is may be advantageous that the configuration in which the distal-side movable bodies 60 have no driving source for rotational operation be applied to a configuration using the type of surgical instrument 70 having only the imaging function.

In the configuration in which the distal-side movable bodies 60 have no driving source for rotational operation, the distal-side movable bodies 60 are not rotated by the driving forces of actuators, so that contact between the movable bodies and the body cavity 201 of the patient 200 at the time of the surgery is sensed easily. Thus, the surgery-assisting device 1 according to some embodiments is easily configured to ensure a force sense presenting function, and an improvement in accuracy of the surgery and an improvement in safety thereof can be achieved.

In the configuration in which the distal-side movable bodies 60 have no driving source for rotational operation, the number of actuators is reduced, and therefore, a reduction in the number of parts and structural simplification can be achieved.

<Modifications of Degrees of Freedom>

Modifications of degrees of freedom will next be described (see FIG. 8).

The above description illustrates example embodiments in which the surgery-assisting device 1 has a configuration with six degrees of freedom. However, embodiments are not limited thereto and, in some embodiments, the surgery-assisting device 1 may, for example, have a configuration with seven degrees of freedom.

Figure 8:
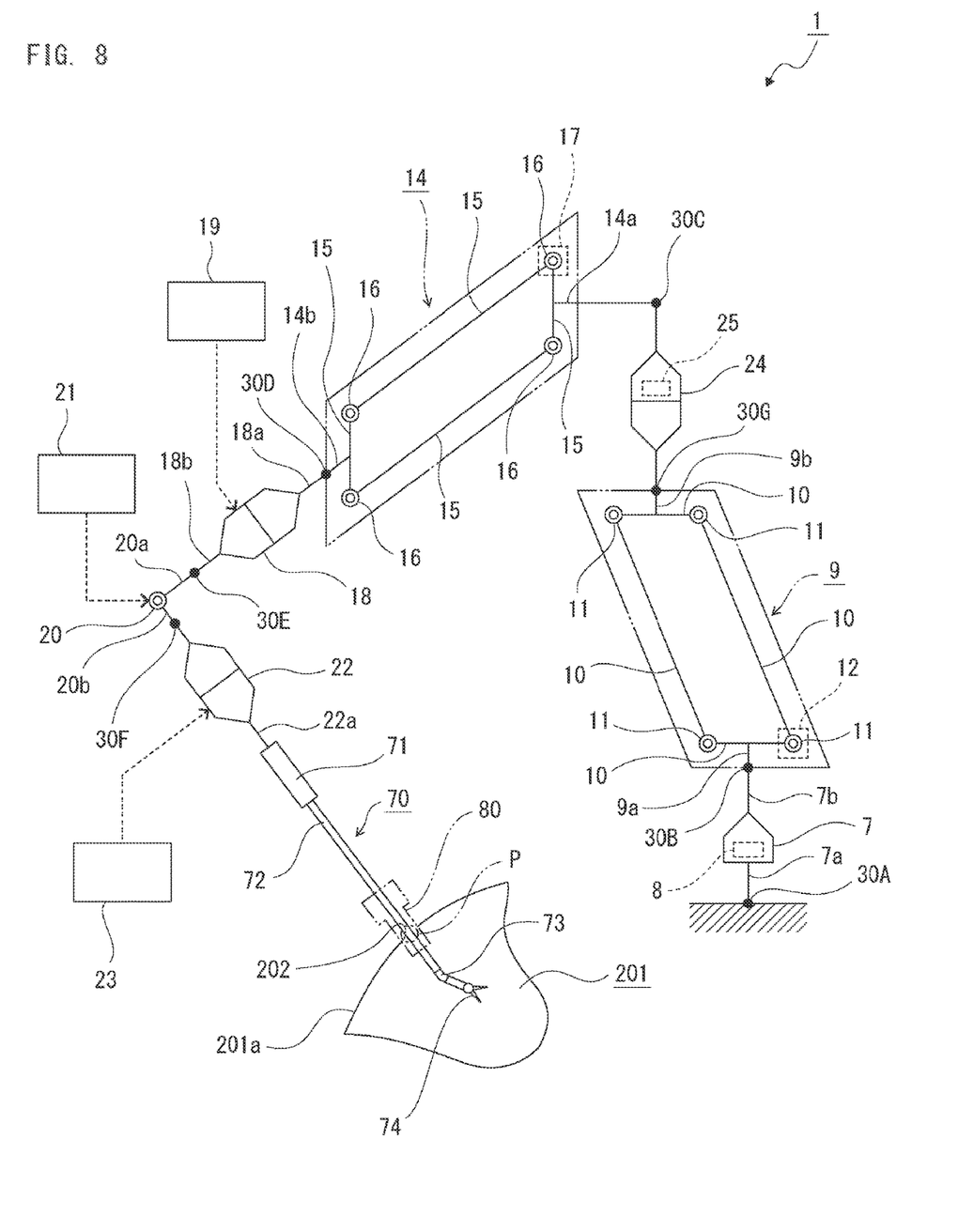
FIG. 8 is a conceptual diagram depicting a surgery-assisting device, according to some embodiments.

FIG. 8 is a conceptual diagram depicting a surgery-assisting device, according to some embodiments. In a case where the surgery-assisting device 1 is configured with seven degrees of freedom, as shown in FIG. 8, a seventh movable body 24, for example, is provided between the second movable body 9 and the third movable body 14. The seventh movable body 24 may be provided in place of the intermediate connecting member 13, for example.

One end portion of the seventh movable body 24 is rotatably connected to the distal end side connecting portion 9b of the second movable body 9. Because of the provision of the seventh movable body 24, a connecting part 30G is formed between the second movable body 9 and the seventh movable body 24. The seventh movable body 24 is, for example, rotated with respect to the second movable body 9 in an axial rotation direction about a reference axis extending in the connecting direction in which the seventh movable body 24 and the second movable body 9 are connected to each other. Hence, because the seventh movable body 24 is rotated with respect to the second movable body 9, the surgery-assisting device 1 has one degree of freedom in an operating direction.

The other end portion of the seventh movable body 24 is rotatably connected to the proximal end side connecting portion 14a of the third movable body 14. A connecting part 30C is formed between the seventh movable body 24 and the third movable body 14. The third movable body 14 is, for example, rotated with respect to the seventh movable body 24 in an axial rotation direction about a reference axis extending in a direction orthogonal to the connecting direction in which the seventh movable body 24 and the third movable body 14 are connected to each other.

A fourth electric actuator 25 that generates a driving force by a motor is disposed in the seventh movable body 24. The seventh movable body 24 is rotated with respect to the second movable body 9 by the driving force of the fourth electric actuator 25. Because the seventh movable body 24 is thus rotated by the driving force of the fourth electric actuator 25, the connecting part 30G between the seventh movable body 24 and the second movable body 9 is held in a secure state by the holding force of the fourth electric actuator 25, and thus has a high stiffness. As with the first movable body 7, the second movable body 9, and the third movable body 14, the seventh movable body 24 is set as a proximal-side movable body 50. Incidentally, the fourth electric actuator 25 may be disposed in the second movable body 9.

In some embodiments, the seventh movable body 24 may be configured to be rotated by the driving force of a pneumatic actuator. In this case, the seventh movable body 24 may be set as a proximal-side movable body 50 or a distal-side movable body 60.

As described with reference to FIG. 8, the plurality of movable bodies each have one degree of freedom in an operating direction, and the surgery-assisting device 1 according to some embodiments may have the configuration with seven degrees of freedom. Thus, operation control performed on each movable body is simplified, and there are more degrees of freedom in operating directions of the surgical instrument 70. It is thus possible to further expand the operating range of the surgical instrument 70 and improve the positional accuracy of the surgical instrument 70 in addition to simplifying operation control on the movable bodies.

In some embodiments, the configuration with seven degrees of freedom may be applied particularly to the surgery-assisting device 1 provided with a plurality of main units 4 (see FIG. 3). For example, in some embodiments, in a case where seven degrees of freedom are applied to the surgery-assisting device 1 provided with two main units 4, in a state in which the operating sections 74 of the surgical instruments 70 are held in substantially the same position and the same pose, the poses of one second movable body 9 and one third movable body 14 can be changed with respect to the poses of the other second movable body 9 and the other third movable body 14 by changing the rotational states of the seventh movable bodies 24.

Hence, even in a state in which the operating sections 74 are held in substantially the same position and the same pose, interference between one main unit 4 and the other main unit 4 can be avoided easily, so that an improvement in safety and an improvement in convenience in the surgery can be achieved.

OTHER MODIFICATIONS

The rotational directions of the first movable body 7, the second movable body 9, the third movable body 14, the fourth movable body 18, the fifth movable body 20, the sixth movable body 22, and the seventh movable body 24 described above are not limited to the directions illustrated in the foregoing, and in some embodiments, the rotational directions may be any directions as long as the surgical instrument 70 can be moved in the three orthogonal axial directions and set in any pose.

In addition, the structures of the first movable body 7, the second movable body 9, the third movable body 14, the fourth movable body 18, the fifth movable body 20, the sixth movable body 22, and the seventh movable body 24 described above each represent an example. In other embodiments, the structures of the first movable body 7, the second movable body 9, the third movable body 14, the fourth movable body 18, the fifth movable body 20, the sixth movable body 22, and the seventh movable body 24 can be of any structure as long as the first movable body 7, the second movable body 9, the third movable body 14, the fourth movable body 18, the fifth movable body 20, the sixth movable body 22, and the seventh movable body 24 are configured to be rotatable.

Further, while the above description illustrates, as an example, the surgery-assisting device 1 having six degrees of freedom or seven degrees of freedom, in some embodiments, the surgery-assisting device 1 may have a configuration in which at least one degree of freedom is ensured by a proximal-side movable body 50, and at least one degree of freedom is ensured by a distal-side movable body 60.

It should be understood that the present disclosure is not limited to the above embodiments, but various other changes and modifications may be made therein without departing from the spirit and scope of the appended claims.

What is claimed is:

1. A surgery-assisting device comprising:
   a plurality of movable bodies that are operably connected in order in a connecting direction; and
   at least one actuator that is configured to generate a driving force that operates at least one of the plurality of movable bodies,
   wherein:
   one of the plurality of movable bodies that is positioned at one end in the connecting direction of the plurality of movable bodies includes a holding portion configured to hold a surgical instrument,
   at least one of the plurality of movable bodies that is positioned on a side of the surgical instrument in the connecting direction and that includes the one of the plurality of movable bodies having the holding portion is provided as a distal-side movable body,
   at least one of the plurality of movable bodies that includes a movable body positioned farthest from the surgical instrument in the connecting direction and that is other than the distal-side movable body is provided as a proximal-side movable body, and
   an operation tolerance of the distal-side movable body is higher than the operation tolerance of the proximal-side movable body, the operation tolerance being a degree of tolerance for operation of a movable body at a time when an external force other than the driving force of the at least one actuator is applied to the movable body.

2. The surgery-assisting device according to claim 1, wherein
   each of the plurality of movable bodies have one degree of freedom in an operating direction of the movable body, and
   a number of the plurality of movable bodies is six to enable operation with six degrees of freedom.

3. The surgery-assisting device according to claim 2, wherein the plurality of movable bodies comprises three proximal-side movable bodies and three distal-side movable bodies.

4. The surgery-assisting device according to claim 1, wherein
   each of the plurality of movable bodies have one degree of freedom in an operating direction of the movable body, and
   a number of the plurality of movable bodies is seven to enable operation with seven degrees of freedom.

5. The surgery-assisting device according to claim 1, wherein:
   the at least one actuator comprises a plurality of actuators, the plurality of actuators include at least one pneumatic actuator configured to generate the driving force by a change in pressure of a gas and at least one electric actuator configured to generate the driving force by a motor,
   the proximal-side movable body is operated by the at least one electric actuator, and
   the distal-side movable body is operated by the at least one pneumatic actuator.

6. The surgery-assisting device according to claim 1, wherein only the proximal-side movable body among the plurality of movable bodies is operated by the at least one actuator.

7. A surgery-assisting device comprising:
   a robot arm comprising a plurality of movable bodies that are operably connected in order in a connection direction;
   a surgical instrument connected to a distal end of the robot arm; and
   at least one actuator that is configured to generate a driving force that operates at least one of the plurality of movable bodies,
   wherein the plurality of movable bodies comprises at least one distal-side movable body that is provided distally in the connection direction, and at least one proximal-side movable body that is provided proximally in the connection direction, and
   wherein an operation tolerance of the at least one distal-side movable body is higher than an operation tolerance of the at least one proximal-side movable body.

8. The surgery-assisting device of claim 7, wherein the operation tolerance is a degree of tolerance for operation of the movable body when an external three other than the driving force is applied to the movable body.

9. The surgery-assisting device of claim 8, wherein the operation is a rotation operation and the operation tolerance is a rotational tolerance.

10. The surgery-assisting device of claim 8, wherein the operation is a rectilinear operation, and the operation tolerance is a rectilinear tolerance.

11. The surgery-assisting device according to claim 7, wherein each of the plurality of movable bodies have one degree of freedom, and a number of the plurality of movable bodies is six to enable operation with six degrees of freedom.

12. The surgery-assisting device according to claim 7, wherein the at least one distal-side movable body comprises a plurality of distal-side movable bodies, and the at least one proximal-side movable body comprises a plurality of proximal-side movable bodies.

13. The surgery-assisting device according to claim 12, wherein a number of the plurality of distal-side movable bodies is equal to a number of the plurality of proximal-side movable bodies.

14. The surgery-assisting device according to claim 12, wherein a number of the plurality of distal-side movable bodies is not equal to a number of the plurality of proximal-side movable bodies.

15. The surgery-assisting device according to claim 7, wherein each of the plurality of movable bodies have one degree of freedom, and a number of the plurality of movable bodies is seven to enable operation with seven degrees of freedom.

16. The surgery-assisting device according to claim 7, wherein the at least one actuator comprises a plurality of actuators, the plurality of actuators include at least one pneumatic actuator and at least one electric actuator,
the at least one proximal-side movable body is operated by the at least one electric actuator, and
the at least one distal-side movable body is operated by the at least one pneumatic actuator.

17. The surgery-assisting device according to claim 7, wherein only the at least one proximal-side movable body among the plurality of movable bodies is operated by the at least one actuator, and the at least one distal-side movable body is not operated by the at least one actuator.

18. A surgery-assisting device comprising:
a robot arm comprising a plurality of sections, each section being one of a joint section or an arm section, a first portion of the plurality of sections being located distally on the robot arm and a second portion of the plurality of sections being located proximally on the robot arm;
a surgical instrument connected to a distal end of the robot arm; and
at least one actuator that is configured to generate a driving force that operates at least one of the plurality of sections,
wherein an operation tolerance of each of one or more sections included in the first portion is higher than an operation tolerance of each of one or more sections included in the second portion such that an external force operates the one or more sections included in the first portion more easily than the external force operates the one or more sections included in the second portion.

19. The surgery-assisting device according to claim 18, wherein the at least one actuator comprises a plurality of actuators,
the plurality of actuators include at least one pneumatic actuator and at least one electric actuator,
one or more sections included in the first portion is operated by the at least one pneumatic actuator, and
one or more section in the second portion is operated by the at least one electric actuator.

20. The surgery-assisting device according to claim 18, where a number of the plurality of sections is six and the first portion includes three sections of the plurality of sections and the second portion includes three sections of the plurality of sections.

* * * * *